United States Patent
Lai et al.

(10) Patent No.: US 10,744,152 B2
(45) Date of Patent: Aug. 18, 2020

(54) APPLICATION OF ASARUM TOTAL POLYSACCHARIDES IN PREPARATION OF MEDICINE FOR TREATING COUGH

(71) Applicants: THE FIRST AFFILIATED HOSPITAL OF GUANGZHOU MEDICAL UNIVERSITY, Guangzhou, Guangdong (CN); GUANGZHOU INSTITUTE OF RESPIRATORY DISEASE, Guangzhou, Guangdong (CN)

(72) Inventors: Kefang Lai, Guangdong (CN); Xiaodong Liu, Guangdong (CN); Bonian Zhong, Guangdong (CN); Shan Zhong, Guangdong (CN); Yichu Nie, Guangdong (CN)

(73) Assignees: THE FIRST AFFILIATTED HOSPITAL OF GUANGZHOU MEDICAL UNIVERSITY, Guangzhou (CN); GUANGZHOU INSTITUTE OF RESPIRATORY DISEASE, Guangzhou (CN)

(*) Notice: Subject to any disclaimer, the term of this patent is extended or adjusted under 35 U.S.C. 154(b) by 188 days.

(21) Appl. No.: 15/996,504

(22) Filed: Jun. 3, 2018

(65) Prior Publication Data

US 2018/0271896 A1 Sep. 27, 2018

Related U.S. Application Data

(60) Division of application No. 15/110,100, filed on Jul. 7, 2016, now abandoned, and a continuation of application No. PCT/CN2015/075054, filed on Mar. 25, 2015.

(30) Foreign Application Priority Data

Mar. 25, 2014 (CN) .......................... 2014 1 0115066

(51) Int. Cl.
A61K 36/00 (2006.01)
A61K 31/715 (2006.01)
A61K 36/268 (2006.01)

(52) U.S. Cl.
CPC .......... *A61K 31/715* (2013.01); *A61K 36/268* (2013.01); *A61K 2236/00* (2013.01); *A61K 2236/30* (2013.01)

(58) Field of Classification Search
CPC ..................................................... A61K 36/00
See application file for complete search history.

(56) References Cited

FOREIGN PATENT DOCUMENTS

| CN | 1459305 A | 12/2003 |
|---|---|---|
| CN | 103202986 A | 7/2013 |
| CN | 104027345 A | 9/2014 |
| JP | 0680577 A | 3/1994 |

OTHER PUBLICATIONS

Li,Jingjing et al.,"Study on the Separation,Purification and Immunological Activity of Polysaccharides from Asarum Heterotropoides",Journal of Changchun Teachers College (Natural Science),Feb. 28, 2008,pp. 54-58.

*Primary Examiner* — Qiuwen Mi
(74) *Attorney, Agent, or Firm* — Wayne & Ken, LLC; Tony Hom

(57) ABSTRACT

The present invention discloses an *Asarum* total polysaccharide extract with antitussive activity, an extraction method thereof and an application in the preparation of a medicine for preventing and treating coughs. The present invention proves that the *Asarum* total polysaccharide extract has a significant effect of suppressing cough for the first time through a large number of pharmacodynamic tests, has the therapeutic effect approximate to codeine, has the effect of prolonging the cough latent period better than codeine, and also finds that the total *Asarum* polysaccharide extract has the effects of reducing the cough sensitivity and suppressing the airway inflammation for the first time, has excellent preventive and therapeutic effects on various types of coughs, and can be used for preparing the medicines for preventing and treating cough-related diseases.

7 Claims, 4 Drawing Sheets

APPLICATION OF ASARUM TOTAL POLYSACCHARIDES IN PREPARATION OF MEDICINE FOR TREATING COUGH

CROSS REFERENCE TO RELATED APPLICATION(S)

This application is a divisional application of U.S. patent application Ser. No. 15/110,100 with a filing date of Jul. 6, 2016. The content of the aforementioned application, including any intervening amendments thereto, is incorporated herein by reference.

TECHNICAL FIELD

The present invention belongs to the technical field of medicines, and more particularly relates to an *Asarum* total polysaccharide extract with antitussive activity as well as an extraction method and an application thereof.

BACKGROUND

Due to the work pressure, air and environment pollution and many other factors, the incidence of human respiratory diseases remains high, while cough is a common and frequently-occurring disease of respiratory system and is a common chief complaint of respiratory outpatient. The cough itself is a defensive reflex activity generated when the respiratory system is stimulated, is a beneficial action, and sometimes is also found in healthy people. In general, mild and infrequent coughs can be relieved naturally without applying antitussive medicines. In addition, impact of the cough on human health is also dialectical and is also a pathological reaction; and long-term frequent or too intense cough not only may increase the suffering of patients, affect the rest and sleep and increase the physical exertion, but also may promote the development of diseases in severe cases to cause other complications.

According to different courses of the disease, the cough can be divided into acute cough, subacute cough and chronic cough. The course of acute cough is less than three weeks, that of subacute cough is three to eight weeks, and that of chronic cough is more than or equal to eight weeks. 1) The acute cough: at present, acute viral upper respiratory tract infection is generally considered as the most common cause, and others include rhinitis, sinusitis, acute bronchitis, acute exacerbation of chronic bronchitis, bronchial asthma and the like; the most common pathogens of upper respiratory tract infection are rhinovirus, coronavirus, respiratory syncytial virus, parainfluenza virus, adenovirus, enterovirus and the like, wherein rhinovirus is most common; the acute cough may also be associated with the acute exacerbation of asthma, bronchitis and other respiratory diseases; and clinically, many infectious diseases or some other diseases having the acute cough as a prodroma can often be seen. 2) The subacute cough: the most common causes are post-infectious cough (also known as post-cold cough), bacterial sinusitis, asthma and the like; a virus as the pathogen is commonly rhinovirus, accounting for about 30%-50%, followed by coronavirus and influenza virus, respectively accounting for 10%45% and 5%-15%; and in addition to respiratory viruses, *mycoplasma pneumoniae, chlamydia pneumoniae* and the like can also cause post-infectious cough. 3) The chronic cough: the chronic cough is usually used for defining a patient having cough as the only symptom or the main symptom, having the course of disease of more than eight weeks and having no apparent abnormality in chest X-ray examination in clinical practice, and is known as unexplained chronic cough, called chronic cough for short; the rate of chronic cough is up to 10%-38% in specialty clinic; questionnaires of European and American countries show that the incidence of chronic cough is also up to 9%-33%; and the common causes of chronic cough are eosinophilic bronchitis (EB), upper airway cough syndrome (UACS, formerly known as postnasal drip syndrome (PNDS)), gastroesophageal reflux cough (GERC), cough variant asthma (CVA) and the like.

A site investigation for the cough of 1087 college students of Guangzhou Institute of Respiratory Diseases in 2006 showed that the overall incidence of cough in groups was 10.9%, wherein the overall incidence of chronic cough was 3.3%. It can be speculated that the incidence of cough in community population may be higher, and the average course of disease of such patients was longer, some even up to decades of years. Some data showed that about 15% of adults and 10% of minors were affected by different degrees of cough all over the world every year. Therefore, the development of safe and effective antitussive medicines can create better social benefits and economic benefits while meeting a huge market demand.

According to different action mechanisms of medicines, the antitussive medicines can be divided into two categories as follows: the first category is centrally acting antitussive medicines; such medicines can directly and selectively inhibit the medullary respiratory center to generate an antitussive effect, such as morphine, codeine, etc.; and such medicines have better antitussive effect, but have obvious side effects, can lead to addiction and respiratory depression, and even induce hallucinations, delusions or other psychotic symptoms. The second category is peripherally acting antitussive medicines; such medicines block the afferent impulse of cough reflex by inhibiting the lung-vagal reflex, thereby playing an antitussive role, such as benproperine, benproperine phosphate, Moguisteine and the like; and most of such medicines are alkaloid medicines, and may cause nausea, palpitation, dizziness or other adverse reactions. Although various medicines can be used for relieving the cough clinically, many patients with chronic cough cannot get effective relief after treatment by using these medicines.

The traditional Chinese medicine is a crystallization of rich practical experience of Chinese people in the prevention and treatment of diseases for thousands of years. Doctors of traditional Chinese medicine may recognize some diseases unknown by doctors of western medicine. The traditional Chinese medicines may be used for treating some diseases refractory and incurable to western medicines. The traditional Chinese medicine has a long history and rich experience in the treatment of coughs, and is complementary with the western medicines used by the doctors of western medicine. Although there are a lot of traditional Chinese medicines and Chinese patent medicines for treating coughs in China at present, the effective components and the indications of these medicines are not clear. In addition, there is no good treatment medicine for patients with unexplained chronic cough and airway inflammation, so the primary task of pharmaceutical workers engaged in the field of respiratory diseases is to research and develop pure natural traditional Chinese medicines which have fewer side effects and can effectively treat coughs.

*Asarum*, as a traditional Chinese medicine, is firstly recorded in the Yellow Emperor's Internal Classic, and is classified as a top grade. 2010 edition of Chinese Pharmacopoeia stipulates that the source of *Asarum* is dried roots and rhizomes of *Asarum Heterotropoides* Fr. Schmidt var.

*Mandshuricum* (Maxim.) Kitag., *Asarum sieboldii* Miq. var. *seoulense* Nakai, or *Asarum sieboldii* Miq. The *Asarum* is warm in nature, acrid in flavor, and attributive to heart, lung and kidney meridians, has the effects of relieving exterior syndrome and dispelling cold, dispelling wind and relieving pain, opening orifices, and warming the lung to dissipate phlegm retention, and is used for treating cough and asthma due to phlegm retention, wind-cold type common cold, headache, toothache, nasal congestion and discharge, allergic rhinitis, nasosinusitis, and Rheumatic arthralgia. Some ancient books record the use of *Asarum* for treating coughs, for example, the Yellow Emperor's Internal Classic records, "the *Asarum* has main indications for cough with dyspnea, headache during use of brains, . . . , and has the effects of freeing nine orifices"; Compendium of Materia *Medica* records, "acrid in flavor can clear lung, so it is suitable for use by patients with wind-cold type common cold and abnormal rising of qi"; Rihuazi Bencao records, "treating coughs, . . . , chest accumulation"; Changsha Yaojie records, "good at reducing adverse rising, designed to stop coughing"; and Medicinal Theory records, "treating cough with dyspnea, . . . ". At present, reports for literature about the antitussive effect of *Asarum* mostly focus on compound methyleugenol of total volatile oil (Zhou Huiqiu, Study on Pharmacological Effects of Methyleugenol, Acta Chinese Medicine and Pharmacology, 2000, (2):79-80). Also, the study on non-volatile components of *Asarum* is rarely reported, and only the isolation of non-volatile constituents, including kakuol, 1-asarinin, 1-sesamin, aristololactam I, kaempferol-3-O-glucoside and the like, from the roots and rhizomes of *Asarum* is reported (Cai Shaoqing, Study on Non-Volatile Chemical Constituents of *Asarum Heterotropoides* Fr. Schmidt var. *Mandshuricum* (Maxim.) Kitag., Journal of Beijing Medical University, 1996, 28(3): 228-230; Lv Shuai, Isolation and identification of chemical constituents from roots of *Asarum Heterotropoides* Fr. Schmidt var. *Mandshuricum* (Maxim.) Kitag. (II), Journal of Shenyang Pharmaceutical University, 2010, 27(9): 707-710; Wei Qingchun, Isolation and Identification of Chemical Constituents of *Asarum sieboldii* Miq. var. *seoulense* Nakai, Li Shizhen Medicine and Materia *Medica* Research, 2010, 21(3): 676-677). A preparation method of *Asarum* polysaccharide has been studied and reported (Li Jingjing, Study on the Separation, Purification and Immunological Activity of Polysaccharide from *Asarum Heterotropoides*, Journal of Changchun Normal University (Natural Science), 2008, 27(1): 54-58), but this preparation method needs to extract three times, the extracting cycle each time is longer (6 hours), and the centrifugation treatment is required in the preparation process, therefore, this method is not suitable for industrial mass production; with adoption of this preparation method, the overall yield of polysaccharides is lower (9.56 wt %), and the content of saccharides is also lower (48 wt % to 52 wt %); in addition, it is reported that *Asarum* polysaccharide, the non-volatile constituent of *Asarum*, has an effect of promoting the proliferation of mouse spleen lymphocytes T and B (Li Jingjing, Study on the Separation, Purification and Immunological Activity of Polysaccharide from *Asarum Heterotropoides*, Journal of Changchun Normal University (Natural Science Edition), 2008, 27(1): 54-58). However, the studies and reports about the antitussive activity of *Asarum* total polysaccharide, the non-volatile constituent of *Asarum*, have not been seen at present.

SUMMARY

In view of the above defects of the prior art, the primary purpose of the present invention is to provide a new application of an *Asarum* total polysaccharide extract in medicines.

The technical solution for achieving the above purpose is as follows.

An application of the *Asarum* total polysaccharide extract in the preparation of a medicine for preventing and treating coughs is provided.

Another purpose of the present invention is to provide a pharmaceutical composition for preventing and treating coughs.

The technical solution for achieving the above purpose is as follows.

A pharmaceutical composition for preventing and treating coughs has active ingredients comprising the *Asarum* total polysaccharide extract.

In one embodiment, the dose form of the pharmaceutical composition is granules, tablets, capsules, pills, dripping pills, effervescent tablets, ointments, syrups, injections, oral liquid, mixtures, tinctures, sustained-release preparations, controlled-release preparations or targeting preparations.

In one embodiment, the percentage content of polysaccharide in the *Asarum* total polysaccharide extract is 60 wt % to 80 wt %.

In one embodiment, the above cough is chronic cough.

Another purpose of the present invention is to provide a method for extracting the *Asarum* total polysaccharide extract. The *Asarum* total polysaccharide extract obtained by the method has good antitussive activity.

The technical solution for achieving the above purpose is as follows.

A method for extracting the *Asarum* total polysaccharide extract comprises the following steps: using a polar solvent for the heat reflux extraction of roots and/or rhizomes of *Asarum*; decompressing, concentrating and drying the obtained material to obtain an *Asarum* total extract; dissolving the *Asarum* total extract in water to obtain an *Asarum* total extract solution; adding ethanol, wherein the volume percentage of the ethanol in the *Asarum* total extract solution is 60%-99%; decompressing and filtering the solution; using an ethanol solution for washing; and decompressing and drying to obtain the *Asarum* total polysaccharide extract.

In one embodiment, the polar solvent is water.

In one embodiment, the weight of the polar solvent is 5-20 times as much as that of the roots and/or rhizomes of *Asarum*.

In one embodiment, the *Asarum* is *Asarum Heterotropoides* Fr. Schmidt var. *Mandshuricum* (Maxim.) Kitag., *Asarum sieboldii* Miq. var. *seoulense* Nakai or *Asarum sieboldii* Miq., preferably *Asarum Heterotropoides* Fr. Schmidt var. *Mandshuricum* (Maxim.) Kitag.

In one embodiment, the volume percentage of the ethanol solution for washing is 60%-100%, and the ethanol solution with the volume percentage of 80%-100% for ethanol washing is preferably adopted for washing.

The method for extracting the *Asarum* total polysaccharide extract with antitussive activity of the present invention has a total polysaccharide yield of 15 wt %.

The use of the above *Asarum* total polysaccharide extract with antitussive activity in the preparation of the medicine for treating coughs is provided. The *Asarum* total polysaccharide extract is used for preparing the medicine for treating coughs individually or in combination with other medicines.

The *Asarum* total polysaccharide extract is prepared into various formulations with available pharmaceutical carriers.

The formulations are granules, tablets, capsules, pills, dripping pills, effervescent tablets, ointments, syrups, injections, oral liquid, mixtures, tinctures, sustained-release preparations, controlled-release preparations or targeting preparations.

The previous study of the inventor of the present invention finds that: *Asarum* volatile oil has an obvious antitussive effect on guinea pig models with acute cough induced by citric acid, but the antitussive effect on guinea pig models with cough hypersensitivity under cigarette smoke (CS) exposure is obviously not better than that of the *Asarum* total polysaccharide, the non-volatile constituent of *Asarum*, and a large dose has a certain side effect.

A pharmacological experiment proves that the *Asarum* total polysaccharide extract has good activity for alleviating and/or inhibiting coughs and can be used for preventing or treating various coughs.

Pharmacodynamic test results show that, for the guinea pig models with acute cough, the low-, medium- and high-dosage groups of *Asarum* total polysaccharide extracts, compared with the blank control group, after citric acid excitation can prolong the cough latent period of the animals and reduce the cough frequency of guinea pigs; compared with the *Asarum* total volatile oil, the acute antitussive activity of *Asarum* total polysaccharide to the guinea pigs is relatively weaker, while for the guinea pig models with cough hypersensitivity and accompanied airway inflammation (CS-exposure for 14 days), the low-, medium- and high-dosage groups of *Asarum* total polysaccharide extracts, compared with the model group, after citric acid excitation can obviously prolong the cough latent period of the animals, reduce the cough frequency of guinea pigs, can also reduce the number of total cells and percentage of neutrophils in BALF of guinea pigs, and inhibit the airway inflammation, thereby achieving or approaching the effects of codeine; compared with the *Asarum* total extract and the *Asarum* total volatile oil, the antitussive rate of the high dose group of *Asarum* total polysaccharide extract has a significant difference ($p<0.05$), which shows that the *Asarum* total polysaccharide extract has better antitussive activity to the guinea pig models with cough hypersensitivity under long-term CS-exposure.

The acute toxicity test results show that, after intragastric administration of the *Asarum* total polysaccharide extract, the SPF grade NIH mice are normal in food intake and weight, and LD50>10.0 g/kg, thereby indicating that the *Asarum* total polysaccharide extract has low toxicity and good medication safety.

The present invention has the beneficial effects:

(1) The present invention provides a new selection and idea for the current antitussive medicine, extends the selection field of the antitussive medicine, and makes contributions to the development of the technical field. The present invention proves that the *Asarum* total polysaccharide extract has an obvious antitussive effect for the first time, and has the functions of reducing cough sensitivity and inhibiting airway inflammation without addiction. The acute toxicity test results show that the *Asarum* total polysaccharide extract has low toxicity and good medication safety.

(2) The preparation process of the *Asarum* total polysaccharide extract provided by the present invention can effectively enrich the total polysaccharide and remove impurities. The yield and the content of the *Asarum* total polysaccharide are high. In quality control, content determination analysis can be performed through ultraviolet spectrophotometry. The method is simple, easy in operation, controllable, and has the advantages of simplicity, quickness, good reproducibility; meanwhile, the solvent adopted is cheap and non-toxic. Especially, the *Asarum* total polysaccharide obtained by the extracting method provided by the present invention has better antitussive activity, and provides more selections of medicines for preventing and treating coughs clinically.

DETAILED DESCRIPTION

Figure 1:
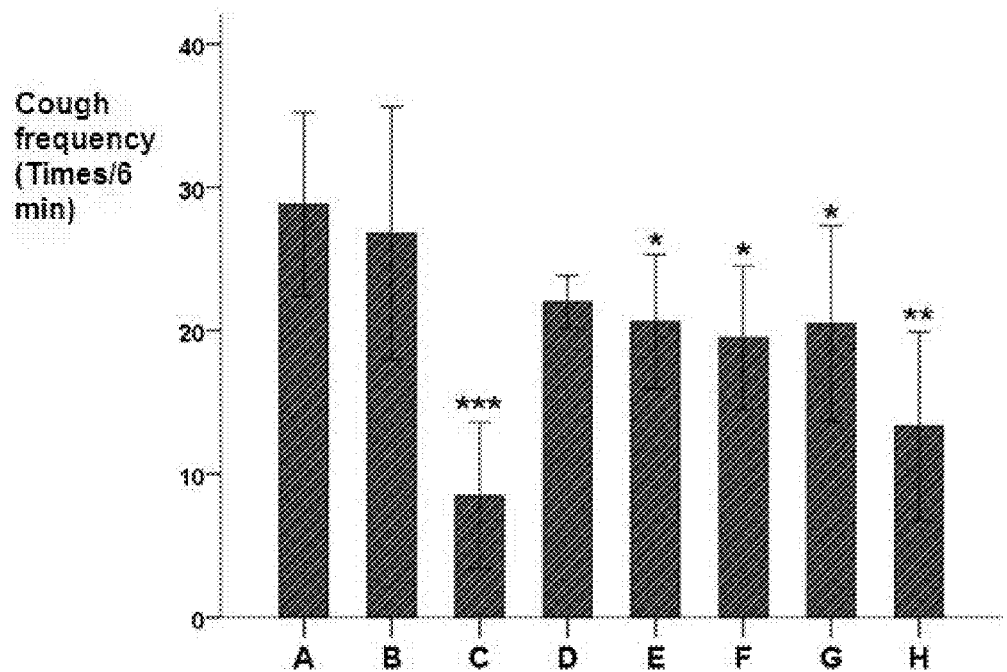
FIG. 1 shows an influence (Mean+/−s, n=8) of *Asarum* total polysaccharide on the cough frequency of guinea pig models with acute cough, wherein A is the blank control group, B is the solvent group (mass fraction 0.5% CMC-Na), C is the codeine phosphate 30 mg/kg group, D is the *Asarum* total polysaccharide 200 mg/kg group, E is the *Asarum* total polysaccharide 400 mg/kg group, F is the *Asarum* total polysaccharide 800 mg/kg group, G is the total *Asarum* extract 1600 mg/kg group, and H is the *Asarum* total volatile oil 200 mg/kg group; and compared with the blank group, *p is less than 0.05, p is less than 0.01, and *p is less than 0.001.
Figure 2:
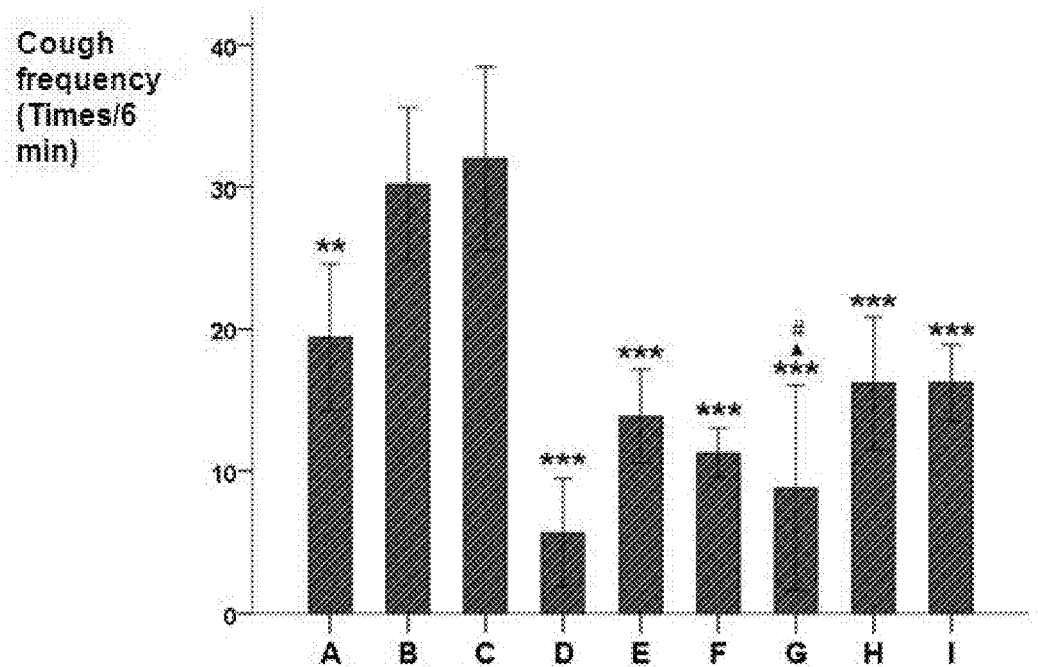
FIG. 2 shows the influence (Mean+/−s, n=8) of *Asarum* total polysaccharide on the cough frequency of guinea pig models with cough hypersensitivity, wherein A is the blank group, B is the model group, C is the solvent group (mass fraction 0.5% CMC-Na), D is the codeine phosphate 30 mg/kg group, E is the *Asarum* total polysaccharide 200 mg/kg group, F is the *Asarum* total polysaccharide 400 mg/kg group, G is the *Asarum* total polysaccharide 800 mg/kg group, H is the total *Asarum* extract 1600 mg/kg group, and I is the *Asarum* total volatile oil 200 mg/kg group; compared with the model group, p is less than 0.01, and *p is less than 0.001; compared with the total *Asarum* extract group, ▲p is less than 0.05; and compared with the *Asarum* total volatile oil group, #p is less than 0.05.

The present invention is further described in detail below in combination with the drawings and specific embodiments, but not regarded as the limitation of the present invention.

In one embodiment, an application of the *Asarum* total polysaccharide extract in the preparation of a medicine for preventing and treating coughs is provided.

In one embodiment, the *Asarum* total polysaccharide extract has a good preventive and therapeutic effect on the acute cough or the chronic cough. The percentage content of effective polysaccharide in the *Asarum* total polysaccharide extract is measured by using an ultraviolet spectrophotometry, using anhydrous glucose as a reference substance, and using a phenol-sulfuric acid method at 490 nm wavelength or using an anthrone method at 620 nm wavelength. The percentage content of polysaccharide is 60 wt % to 80 wt %; and a polysaccharide sample is hydrolyzed and derived, and then is measured to contain glucose, mannose, arabinose, galactose, xylose, rhamnose, ribose and galacturonic acid through GC-MS measurement.

In one embodiment, a pharmaceutical composition for preventing and treating coughs has active ingredients comprising *Asarum* total polysaccharide extract with the polysaccharide percentage content of 60 wt % to 80 wt %, and can also be combined with other medicines with antitussive activity. The active ingredients further comprise a pharmaceutically acceptable carrier, such as fillers, adhesives, lubricants, disintegrants or wetting agents, wherein the fillers comprise lactose, sucrose, corn starch and sorbitol; the adhesives comprise syrup, arabic gum, gelatin, sorbitol, hydroxypropyl methylcellulose or polyvinylpyrrolidone; the lubricants comprise magnesium stearate; the disintegrants comprise starch, polyvinylpyrrolidone, crospovidone and microcrystalline cellulose; and the wetting agents comprise sodium dodecyl sulfate.

In one embodiment, the formulations of the pharmaceutical composition are granules, tablets, capsules, pills, dripping pills, effervescent tablets, ointments, syrups, injections, oral liquid, mixtures, tinctures, sustained-release preparations, controlled-release preparations or targeting preparations.

In one embodiment, the effective dose of the *Asarum* total polysaccharide extract with antitussive activity, calculated according to the weight of a person of 60 kg, is 2.5 g-11.0 g per person per day.

A method for extracting the *Asarum* total polysaccharide extract with antitussive activity of the present embodiment comprises the following steps: using a polar solvent for the heat reflux extraction of roots and/or rhizomes of *Asarum*, wherein the polar solvent is preferably water, and the weight of the polar solvent is 5-20 times as much as that of the roots and/or rhizomes of *Asarum*; then, decompressing, concentrating and drying the obtained material to obtain an *Asarum* total extract; next, dissolving the *Asarum* total extract in water; using an ethanol solution with the ethanol volume percentage of 40%-99% (preferably 60%-90% or preferably 60%-99%) for precipitation; decompressing and filtering the solution; using the ethanol solution (with the ethanol volume percentage of 60%-100%, the ethanol solution or ethanol with the ethanol volume percentage of 80%-100% is more preferably used in the present embodiment) for washing precipitates for 1-3 times, preferably 2 times; and then decompressing and drying the precipitates to obtain the *Asarum* total polysaccharide extract.

The *Asarum* is *Asarum Heterotropoides* Fr. Schmidt var. *Mandshuricum* (Maxim.) Kitag., *Asarum sieboldii* Miq. var. *seoulense* Nakai or *Asarum sieboldii* Miq., preferably *Asarum Heterotropoides* Fr. Schmidt var. *Mandshuricum* (Maxim.)Kitag. in the present embodiment.

The method for extracting the *Asarum* total polysaccharide extract with antitussive activity of the present invention has a total polysaccharide yield of 15 wt %. The *Asarum* total polysaccharide extract obtained by the above method has a better antitussive effect.

The following is the part of the specific embodiments, for illustrating the present invention in more detail, but not limiting the protection scope of the present invention.

Embodiment 1

A method for preparing the *Asarum* total polysaccharide extract of the present embodiment comprises the following steps:

Crushing 1 kg of dried roots and/or rhizomes of *Asarum Heterotropoides* Fr. Schmidt var. *Mandshuricum* (Maxim.) Kitag. into coarse powder; screening the coarse powder with a sieve of 80 meshes; using water being 10 times as much as the weight of medicinal materials for slight-boiling heating and reflux extraction for 5 hours; filtering an extracting solution with 6 layers of gauze; decompressing, concentrating and drying the filtrate to obtain the *Asarum* total extract;

Using water for heating and dissolving the *Asarum* total extract to be 1 L; adding 9 times volume of anhydrous ethanol until the volume percentage concentration of ethanol is 90% while stirring; stewing the mixture in a refrigerator at 4° C. after full precipitation; pouring supernatant; decompressing and filtering the precipitates; using the same amount of ethanol aqueous solution with the volume percentage of 90% for washing twice; drying the obtained material conventionally to obtain the *Asarum* total polysaccharide extract, wherein the yield is 15 wt %. The contents of *Asarum* total polysaccharide measured by ultraviolet spectrophotometry using the phenol-sulfuric acid method and the anthrone method respectively are 68 wt % and 60 wt %.

Embodiment 2

A method for preparing the *Asarum* total polysaccharide extract of the present embodiment comprises the following steps:

Crushing 1 kg of dried roots and/or rhizomes of *Asarum Heterotropoides* Fr. Schmidt var. *Mandshuricum* (Maxim.) Kitag. into coarse powder; screening the coarse powder with a sieve of 80 meshes; using water being 10 times as much as the weight of medicinal materials for slight-boiling heating and reflux extraction for 5 hours; filtering the extracting solution with 6 layers of gauze; and decompressing, concentrating and drying the filtrate to obtain the *Asarum* total extract;

Using water for heating and dissolving the *Asarum* total extract to be 1 L; adding 15 times volume of anhydrous ethanol until the volume percentage concentration of ethanol is 94% while stirring; stewing the mixture in the refrigerator at 4° C. after full precipitation; pouring supernatant; decompressing and filtering the precipitates; using the same amount of ethanol aqueous solution for washing three times; and drying the obtained material conventionally to obtain the *Asarum* total polysaccharide extract, wherein the yield is 13 wt %. The contents of *Asarum* total polysaccharide measured by ultraviolet spectrophotometry using the phenol-sulfuric acid method and the anthrone method respectively are 75 wt % and 70 wt %. A polysaccharide sample is hydrolyzed and derived, and then is measured to contain glucose, mannose, arabinose, galactose, xylose, rhamnose, ribose and galacturonic acid through GC-MS measurement.

Embodiment 3

Test for acute toxicity of *Asarum* total polysaccharide extract orally and intragastrically administered to mice.

1. Animals

SPF grade NIH mice, including half males and half females, weighing 18-22 g, being provided by the Guangdong Medical Laboratory Animal Center, having an animal certificate number of SCXK (Guangdong province, China) 2008-0002.

2. Method

The acute toxicity of *Asarum* total polysaccharide extract orally and intragastrically administered to mice is investigated by referring to the Experimental Methodology of Pharmacology and the Experimental Methodology of TCM Pharmacology and using a normal Bliss method. Firstly, the maximum concentration, the maximum administration dose and the maximum intragastric administration volume are used for testing. Before the test, the mice are subjected to food-fasting but not water-fasting for 12 hours; and when the test is carried out, 10.0 g/kg of *Asarum* total polysaccharide extract (obtained according to the preparation method described in the Embodiment 1) is intragastrically administered to the mice (equivalent to 24.4 g/kg of crude medicine, equivalent to 12 times as much as the clinical dose). The laboratory temperature is 25+/−2° C.; the observation is kept for 14 days after once administration; each animal is observed carefully, and the appearing and disappearing time of various toxicities are recorded in detail. Observed and recorded contents include behavioral expressions of skin, mucosa, hair color, eyes, respiration, circulation, locomotor activity, central nervous system and the like. The animals should be weighed within a week before and after administering a test substance, when the animals die and the test is ended. The autopsy should be conducted on all animals, including animals which die or are killed; and the histopathological examination should be conducted on organs abnormal in autopsy.

3. Results

The test results show that 10.0 g/kg of *Asarum* total polysaccharide extract is orally and intragastrically administered to the mice, no animal dies within 14 days after administration, the mental and behavioral activities of all animals are in good condition, the skin and the hair are clean, the defecation and the increases of weight and food intake are normal, and no other symptom of toxicity is found. No obvious organ abnormality is found in gross anatomy after the end of observation. LD50 of the *Asarum* total polysaccharide is more than 10.0 g/kg.

The above results indicate that the *Asarum* total polysaccharide has high safety and has no risk of severe acute poisoning.

Embodiment 4

Acute antitussive effect of *Asarum* total polysaccharide extract on cough of guinea pigs induced by citric acid 1. Materials Animals: ordinary grade Hartley guinea pigs, including half males and half females, weighing 250-350 g, being provided by the Guangdong Medical Laboratory Animal Center, having the animal certificate number of SCXK (Guangdong province, China) 2008-0002.

Reagent and Instruments: citric acid monohydrate (Guangzhou Chemical Reagent Factory, Batch Number: 20121001-2), which is prepared into a normal saline solution of 0.8 M when use; a Buxco noninvasive animal pulmonary function testing system (US Buxco Company); an Aeroneb Pro nebulizer (Aerogen (Ireland) Co., Ltd.); and an intragastric administration needle (Guangdong Medical Laboratory Animal Center).

2. Method

A guinea pig acute cough model induced by citric acid is used for the efficacy evaluation. 128 Hartley guinea pigs are taken and are placed in a 6 L body plethysmograph of the Buxco noninvasive animal pulmonary function testing system one by one; the air flow rate of a bias meter is 2.5 L/min; the Aeroneb Pro nebulizer is used for feeding nebulized citric acid ultrapure aqueous solution aerosol of 0.8 M for 1 min, wherein the average diameter of nebulized particles is 2.5 μm; the observation is kept for 5 min, to monitor the cough frequency within 6 min; the sound of cough is recorded and amplified by a microphone placed indoors; sound waves are analyzed through Biosystem XA software; the sound data are processed by the computer software to record the cough frequency; and meanwhile, a trained observer carries out supplementary observation. The guinea pigs with the cough frequency of more than 10 times are selected as qualified animals for testing.

64 screened and qualified Hartley guinea pigs, including half males and half females, are taken and randomly divided into eight groups; the blank group is administered with 1 mL/kg of normal saline; the solvent group is administered with the same volume of corresponding solvent (a CMC-Na aqueous solution with the mass percentage concentration of 0.5%); a positive medicine group is administered with the same volume of 30 mg/kg of codeine phosphate; and the administration groups are administered with the same volume of *Asarum* total polysaccharide extract (200 mg/kg, 400 mg/kg and 800 mg/kg of samples in the Embodiment 1), *Asarum* total extract (1600 mg/kg), *Asarum* total volatile oil (200 mg/kg, prepared by conventional steam distillation), once a day for consecutive 3 days. A citric acid nebulization excitation test (nebulization conditions are the same as above) is conducted in the Buxco noninvasive animal pulmonary function testing system within 2 hours after the last administration; the nebulization excitation is conducted for 1 min to induce the guinea pigs to have acute cough; the observation is kept for 5 min; the cough frequency (N) within 6 min and a cough latent period are calculated; and the antitussive rate of each administration group is calculated by using the formula "the antitussive rate=(Nblank control group−Nadministration group)/Nblank control group×100%".

Data are represented by mean+/−s. The statistical software IBM SPSS Statistics 19.0 is used for the one-way analysis of variance of each group of parameters. In the comparison between groups, if p is less than 0.05, there is a significant difference.

3. Results (1) Influence of *Asarum* Total Polysaccharide Extract on the Cough Frequency of Guinea Pig Models with Acute Cough The cough frequency and the cough suppression rate of animals in each group within 6 min after the citric acid nebulization excitation are shown in Table 1 and FIG. 1. Table 1 and FIG. 1 show that, compared with the blank group, the medium- and the high-dosage groups of *Asarum* total polysaccharide extract both can significantly reduce the cough frequency of guinea pigs (p<0.05), and have the antitussive rates up to 28.5% and 32.3%, respectively. When the dose of *Asarum* total extract is 1600 mg/kg, the antitussive rate is 28.8%, while the antitussive rate of the high-dosage group of *Asarum* total polysaccharide extract reaches a considerable level when the dose is 800 mg/kg, thereby indicating that the antitussive activity of the *Asarum* total polysaccharide extract is higher than that of the *Asarum* total extract, and further explaining that the *Asarum* total polysaccharide is one of the main active ingredients of the *Asarum* for relieving cough, and there is no significant difference between the *Asarum* total polysaccharide extract and the *Asarum* total extract. The acute antitussive activity (the antitussive rate is 53.8%) of *Asarum* total volatile oil on the guinea pigs is better than that of the *Asarum* total extract and the *Asarum* total polysaccharide, but there is no significant difference among the three.

The above results indicate that the *Asarum* total polysaccharide extract has a good acute antitussive effect, has a dose-effect relationship, and is relatively safe in medication.

TABLE 1

Influence (mean +/− s, n = 8) of *Asarum* total polysaccharide extract on the cough frequency of guinea pig models with acute cough

| Group | Dose (mg/kg) | Cough frequency (times) | Antitussive rate (%) |
|---|---|---|---|
| Blank control | — | 28.8 +/− 3.2 | — |
| Solvent control | — | 26.8 +/− 4.4 | — |
| Codeine phosphate | 30 | 8.5 +/− 2.6*** | 70.5 |
| Low dose of *Asarum* total polysaccharide | 200 | 22.0 +/− 0.9 | 21.5 |
| Medium dose of *Asarum* total polysaccharide | 400 | 20.6 +/− 2.3* | 28.5 |
| High dose of *Asarum* total polysaccharide | 800 | 19.5 +/− 2.5* | 32.3 |
| *Asarum* total extract | 1600 | 20.5 +/− 3.4* | 28.8 |
| *Asarum* total volatile oil | 200 | 13.3 +/− 3.3** | 53.8 |

Note:
compared with the blank group,
*p < 0.05,
**p < 0.01,
***p < 0.001.

(2) Influence of *Asarum* Total Polysaccharide Extract on the Cough Latent Period of Guinea Pig Models with Acute Cough The cough latent period of animals in each group within 6 min after the citric acid nebulization excitation is shown in Table 2. Table 2 shows that, compared with the blank control group, different dose groups of *Asarum* total polysaccharide extract can significantly prolong the cough latent period of the guinea pigs, wherein p is less than 0.05 in the low-dosage group; p is less than 0.01 in the medium- and the high-dosage groups; and the *Asarum* total polysaccharide extract has the dose-effect relationship. Effects of different dose groups of *Asarum* total polysaccharide extract for prolonging the cough latent period are better than the effect of codeine phosphate. The *Asarum* total extract and the *Asarum* total volatile oil may also prolong the cough latent period, but compared with the blank group, there is no statistical significance (p>0.05).

TABLE 2

Influence (mean +/− s, n = 8) of *Asarum* total polysaccharide extract on cough latent period of guinea pig models with acute cough

| Group | Dose (mg/kg) | Cough latent period (seconds) |
|---|---|---|
| Blank control | — | 45.8 +/− 6.2 |
| Solvent control | — | 43.7 +/− 16.8 |
| Codeine phosphate | 30 | 95.3 +/− 18.3 |
| Low dose of *Asarum* total polysaccharide | 200 | 118.9 +/− 24.7* |
| Medium dose of *Asarum* total polysaccharide | 400 | 133.3 +/− 29.5** |

TABLE 2-continued

Influence (mean +/− s, n = 8) of *Asarum* total polysaccharide extract on cough latent period of guinea pig models with acute cough

| Group | Dose (mg/kg) | Cough latent period (seconds) |
|---|---|---|
| High dose of *Asarum* total polysaccharide | 800 | 140.9 +/− 19.7** |
| *Asarum* total extract | 1600 | 106.4 +/− 21.3 |
| *Asarum* total volatile oil | 200 | 100.2 +/− 6.4 |

Note:
compared with the blank group,
*p < 0.05,
**p < 0.01.

Embodiment 5

Antitussive effect of *Asarum* total polysaccharide on guinea pig models with cough hypersensitivity 1. Materials Animals: ordinary grade Hartley guinea pigs, including half males and half females, weighing 250-350 g, being provided by the Guangdong Medical Laboratory Animal Center, having the animal certificate number of SOCK (Guangdong province, China) 2008-0002.

Reagent and Instruments: citric acid monohydrate (Guangzhou Chemical Reagent Factory, Batch Number: 20121001-2), which is prepared into the normal saline solution of 0.8 M when use; the Buxco noninvasive animal pulmonary function testing system (US Buxco Company); the Aeroneb Pro nebulizer (Aerogen (Ireland) Co., Ltd.); a cell counting chamber (Zhejiang Yuhuan County Chumen Medical Instrument Factory); and the intragastric administration needle (Guangdong Medical Laboratory Animal Center).

2. Method

The method for screening qualified animals is the same as that described in the Embodiment 3. 72 screened and qualified animals are taken and are randomly divided into nine groups; the blank group and the model group are administered with 1 mL/kg of normal saline; the solvent group is administered with the same volume of corresponding solvent (the CMC-Na aqueous solution with the mass percentage concentration of 0.5%); the positive medicine group is administered with the same volume of 30 mg/kg of codeine phosphate; the administration groups are administered with the same volume of *Asarum* total polysaccharide extract (200 mg/kg, 400 mg/kg and 800 mg/kg of samples in the Embodiment 1), *Asarum* total extract (1600 mg/kg), *Asarum* total volatile oil (200 mg/kg, prepared by conventional steam distillation), and are intragastrically administered once a day for consecutive 14 days. Except the blank control group, each group is smoked by 10 cigarettes Hongmei (China Tobacco Guangdong Industrial Co., Ltd., tar 13 mg, nicotine 1.3 mg, carbon monoxide 15 mg) for 20 min every time, twice a day for consecutive 14 days; and an efficacy evaluation model for guinea pigs with chronic cough is built. The citric acid nebulization excitation is conducted for 1 min (the Buxco noninvasive animal pulmonary function testing system, the nebulization conditions is the same as those in the Embodiment 3) within 24 hours after the last smoking exposure, to induce the guinea pigs to have a cough; the observation is kept for 5 min; and the cough frequency (N) within 6 min, the antitussive rate and the cough latent period are calculated. Sodium pentobarbital with the mass percentage concentration of 3% is used for anesthetization within 24 hours after the animals are excited; the blood is collected from the heart; 6 mL of ice PBS is used for the bronchoalveolar lavage (BALF) of guinea pigs; and meanwhile, the lung tissues and the tracheal tissues are taken and are fixed with 10% of formaldehyde.

Observation Method and Indicators:

(1) Calculating the cough frequency within 6 min after citric acid excitation, and calculating the antitussive rate of each administration group by using the formula "the antitussive rate=(Nmodel group−Nadministration group)/Nmodel group×100%".

(2) Calculating the cough latent period of each administration group within 6 min after citric acid excitation;

(3) Airway inflammation indicators: <1> total cell count (TCC) in BALF: taking 0.5 mL of BALF fluid after 24 hours following the end of nebulization excitation to centrifuge at 3000 r/min for 10 min, adding 0.3 mL of erythrocyte lysate to the precipitates, shaking and mixing the mixture uniformly, stewing the mixture for 10 min, centrifuging the mixture at 3000 r/min for 10 min, using 0.5 mL of PBS for suspending the precipitates, and taking the cell counting chamber under 10 μL optical microscope to count the TCC; <2> classification of cells in BALF: washing fixed BALF cell smears with running water for 5 min, using hematoxylin for staining 20 seconds, washing the stained cell smears with running water for 5 min, using 1% of hydrochloric acid alcohol for destaining 5 seconds, washing the destained cell smears with running water for 5 min, using eosin for staining 5 seconds, washing the stained cell smears with running water for 5 min, using neutral balsam for mounting after drying the cell smears, and classifying the cells under the optical microscope; and <3> histopathological observation of the lung tissues and the tracheal tissues: conducting HE staining on the lung tissues and the tracheal tissues, wherein for the lung tissues, it is mainly observed that whether bronchi, alveoli and accompanying arterioles are complete in structure, whether ciliated epithelia of the airway are arranged in order, and whether there are inflammatory cells for infiltration around blood vessels, hyperemia and edema and the like; for the tracheal tissues, it is mainly observed that whether the epithelia are complete, whether the lumina are neat and clean, whether the tracheal wall is thickened, and whether the cilia are arranged regularly, fall off, are infiltrated by inflammatory cells and the like.

3. Results (1) Influence of *Asarum* Total Polysaccharide Extract on the Cough Frequency of Guinea Pig Models with Cough Hypersensitivity Compared with the blank group, the cough frequency of guinea pigs in the model group within 6 min after citric acid nebulization excitation and CS-exposure for 14 days is significantly increased ($p<0.01$), so the guinea pigs with cough hypersensitivity are modeled successfully. Compared with the model group, the low-, medium- and high-dosage groups of *Asarum* total polysaccharide extract may significantly reduce the cough frequency of guinea pigs ($p<0.001$), and have the antitussive rates up to 54.0%, 62.6% and 70.9%, respectively. Compared with the *Asarum* total extract and the *Asarum* total volatile oil, the antitussive rate of the high-dosage group of *Asarum* total polysaccharide extract has a significant difference ($p<0.05$). Compared with the codeine phosphate, the antitussive rate of the high-dosage group of *Asarum* total polysaccharide extract has no significant difference, thereby showing that the *Asarum* total polysaccharide extract has better antitussive activity to the guinea pig models with cough hypersensitivity (the results are shown in Table 3 and FIG. 3).

The above results indicate that the *Asarum* total polysaccharide extract has the effect of treating the guinea pigs with chronic cough hypersensitivity, and has the dose-effect relationship, wherein the treatment effect of the high-dosage group of *Asarum* total polysaccharide extract is approximate to that of codeine.

TABLE 3

Influence (mean +/− s, n = 8) of *Asarum* total polysaccharide extract on the cough frequency of guinea pig models with cough hypersensitivity

| Group | Dose (mg/kg) | Cough frequency (times) | Antitussive rate (%) |
|---|---|---|---|
| Blank control | — | 19.4 +/− 2.6** | — |
| Model group | — | 30.2 +/− 2.7 | — |
| Solvent control | — | 32.0 +/− 3.2 | — |
| Codeine phosphate | 30 | 5.7 +/− 1.9*** | 81.1 |
| Low dose of *Asarum* total polysaccharide | 200 | 13.9 +/− 1.7*** | 54.0 |
| Medium dose of *Asarum* total polysaccharide | 400 | 11.3 +/− 0.9*** | 62.6 |
| High dose of *Asarum* total polysaccharide | 800 | 8.8 +/− 3.6***<▲ #> | 70.9 |
| *Asarum* total extract | 1600 | 16.2 +/− 2.3*** | 46.4 |
| *Asarum* total volatile oil | 200 | 16.2 +/− 1.4*** | 46.4 |

Note:
compared with the model group,
**$p < 0.01$,
***$p < 0.001$; compared with the *Asarum* total extract group,
<▲>$p < 0.05$; andcompared with the *Asarum* total volatile oil group,
<#>$p < 0.05$.

(2) Influence of *Asarum* Total Polysaccharide Extract on the Cough Latent Period of Guinea Pig Models with Cough Hypersensitivity The cough latent period of animals in each group within 6 min after the citric acid nebulization excitation and after the cigarette exposure for 14 days is shown in Table 4. Table 4 shows that, compared with the model group, different dose groups of *Asarum* total polysaccharide extract can significantly prolong the cough latent period of the guinea pigs, wherein p is less than 0.001 in the medium- and high-dosage groups, the *Asarum* total polysaccharide extract has the dose-effect relationship, and compared with the codeine phosphate group, the medium- and high-dosage groups have no significant difference, thereby showing that the influence of *Asarum* total polysaccharide extract on the cough latent period is approximate to the effect of codeine phosphate. Compared with the *Asarum* total extract and the *Asarum* total volatile oil, the cough latent period of the high-dosage group of *Asarum* total polysaccharide extract has a significant difference ($p>0.05$).

TABLE 4

Influence (mean +/− s, n = 8) of *Asarum* total polysaccharide extract on the cough latent period of guinea pig models with cough hypersensitivity

| Group | Dose (mg/kg) | Cough latent period (seconds) |
|---|---|---|
| Blank control | — | 61.2 +/− 6.0 |
| Model group | — | 45.2 +/− 4.0 |
| Solvent control | — | 33.6 +/− 3.9 |

TABLE 4-continued

Influence (mean +/− s, n = 8) of
*Asarum* total polysaccharide extract on the cough
latent period of guinea pig models with cough hypersensitivity

| Group | Dose (mg/kg) | Cough latent period (seconds) |
|---|---|---|
| Codeine phosphate | 30 | 199.7 +/− 37.7*** |
| Low dose of *Asarum* total polysaccharide | 200 | 100.3 +/− 17.8 |
| Medium dose of *Asarum* total polysaccharide | 400 | 156.1 +/− 25.0*** |
| High dose of *Asarum* total polysaccharide | 800 | 189.0 +/− 20.4***<▲ #> |
| *Asarum* total extract | 1600 | 117.7 +/− 16.0* |
| *Asarum* total volatile oil | 200 | 112.0 +/− 7.0* |

Note:
compared with the model group,
*$p < 0.05$,
***$p < 0.001$; compared with the *Asarum* total extract group,
<▲>$p < 0.05$; and compared with the *Asarum* total volatile oil group,
<#>$p < 0.05$.

(3) Influence of *Asarum* Total Polysaccharide Extract on TCC in BALF of Guinea Pig Models with Cough Hypersensitivity Compared with the blank group, the TCC in BALF of the model group after CS-exposure for 14 days is significantly increased ($p<0.05$), thereby modeling successfully. Compared with the model group, different dose groups of *Asarum* total polysaccharide extract can reduce the number of total cells in BALF of guinea pigs, wherein the low-dosage group has a better significant difference ($p<0.01$); the medium- and high-dosage groups have significant differences ($p<0.001$) and have the dose-effect relationship. Compared with the *Asarum* total extract and the *Asarum* total volatile oil, the TCC of the medium- and high-dosage groups of *Asarum* total polysaccharide extract has a significant difference ($p<0.05$). Codeine phosphate cannot reduce the total number of inflammatory cells in BALF of airway hypersensitivity guinea pigs with airway inflammation (see Table 5).

TABLE 5

Influence (mean +/− s, n = 8) of *Asarum* total
polysaccharide extract on TCC in BALF of guinea pig models
with cough hypersensitivity

| Group | Dose (mg/kg) | TCC ($\times 10^{<5>}$, cells/mL) |
|---|---|---|
| Blank control | — | 10.8 +/− 2.7*** |
| Model group | — | 27.8 +/− 1.2 |
| Solvent control | — | 26.1 +/− 1.3 |
| Codeine phosphate | 30 | 26.5 +/− 5.9 |
| Low dose of *Asarum* total polysaccharide | 200 | 16.5 +/− 5.2** |
| Medium dose of *Asarum* total polysaccharide | 400 | 8.1 +/− 0.6***<▲ #> |
| High dose of *Asarum* total polysaccharide | 800 | 7.8+/−0.6***<▲ #> |
| *Asarum* total extract | 1600 | 16.1 +/− 1.2** |
| *Asarum* total volatile oil | 200 | 17.6 +/− 2.3* |

Note:
compared with the model group,
*$p < 0.05$,
**$p < 0.01$,
***$p < 0.001$; compared with the *Asarum* total extract group,
<▲>$p < 0.05$; and compared with the *Asarum* total volatile oil group,
<#>$p < 0.05$.

(4) Influence of *Asarum* Total Polysaccharide Extract on the Classification of Cells in BALF of Guinea Pig Models with Cough Hypersensitivity Compared with the blank group, the ratios of macrophages (Mac) in BALF of the model group and the solvent control group after CS-exposure for 14 days are significantly reduced, while the ratios of neutrophils (Neu) are significantly increased, and the ratios have a significant difference ($p<0.001$), which indicates the successful modeling. Compared with the model group, different dose groups of *Asarum* total polysaccharide extract can reduce the ratio of Neu in BALF of the guinea pigs, and have the dose-effect relationship, wherein the high-dosage group has a better significant difference ($p<0.01$); meanwhile, all dose groups of *Asarum* total polysaccharide extract can increase the ratio of Mac, wherein the high-dosage group has a better significant difference ($p<0.01$); compared with the *Asarum* total extract and the *Asarum* total volatile oil, the high-dosage group of *Asarum* total polysaccharide extract can significantly reduce the ratio of Neu; and codeine phosphate cannot reduce the ratio of inflammatory cells in BALF of airway hypersensitivity guinea pigs with airway inflammation (see Table 6).

TABLE 6

Influence (mean +/− s, n = 8) of *Asarum* total polysaccharide extract
on the classification of cells in BALF of guinea pig models with cough hypersensitivity

| Group | Dose (mg/kg) | Mac % | Neu % | Lym % | Eos % |
|---|---|---|---|---|---|
| Blank control | — | 77.0 +/− 1.0*** | 13.3 +/− 0.7*** | 8.4 +/− 1.1 | 1.3 +/− 0.3 |
| Model group | — | 46.5 +/− 1.7 | 44.4 +/− 1.7 | 7.1 +/− 0.8 | 2.1 +/− 0.7 |
| Solvent control | — | 46.9 +/− 3.4 | 46.4 +/− 2.7 | 4.7 +/− 0.7 | 2.0 +/− 0.7 |
| Codeine phosphate | 30 | 39.4 +/− 7.1 | 51.8 +/− 8.4 | 5.3 +/− 1.1 | 3.6 +/− 3.1 |
| Low dose of *Asarum* total polysaccharide | 200 | 48.0 +/− 2.7 | 42.2 +/− 2.5 | 6.1 +/− 1.3 | 3.7 +/− 0.8 |
| Medium dose of *Asarum* total polysaccharide | 400 | 51.6 +/− 4.5<▲> | 37.2 +/− 2.9 | 7.6 +/− 1.8 | 3.5 +/− 0.7 |

TABLE 6-continued

Influence (mean +/− s, n = 8) of *Asarum* total polysaccharide extract
on the classification of cells in BALF of guinea pig models with cough hypersensitivity

| Group | Dose (mg/kg) | Mac % | Neu % | Lym % | Eos % |
|---|---|---|---|---|---|
| High dose of *Asarum* total polysaccharide | 800 | 61.9 +/− 1.5\*\*<▲▲▲#> | 29.4 +/− 0.9\*\*<▲ #> | 7.1 +/− 2.1 | 1.6 +/− 0.4 |
| *Asarum* total extract | 1600 | 42.6 +/− 0.9 | 41.6 +/− 2.1 | 10.8 +/− 1.8 | 5.0 +/− 0.9 |
| *Asarum* total volatile oil | 200 | 50.9 +/− 4.0 | 40.7 +/− 5.4 | 6.3 +/− 1.5 | 2.1 +/− 1.1 |

Note:
compared with the model group,
\*\*$p < 0.01$,
\*\*\*$p < 0.001$; compared with the *Asarum* total extract group,
<▲>$p < 0.05$,
<▲▲▲>$p < 0.001$; and compared with the *Asarum* total volatile oil group,
<#>$p < 0.05$.

Figure 3:
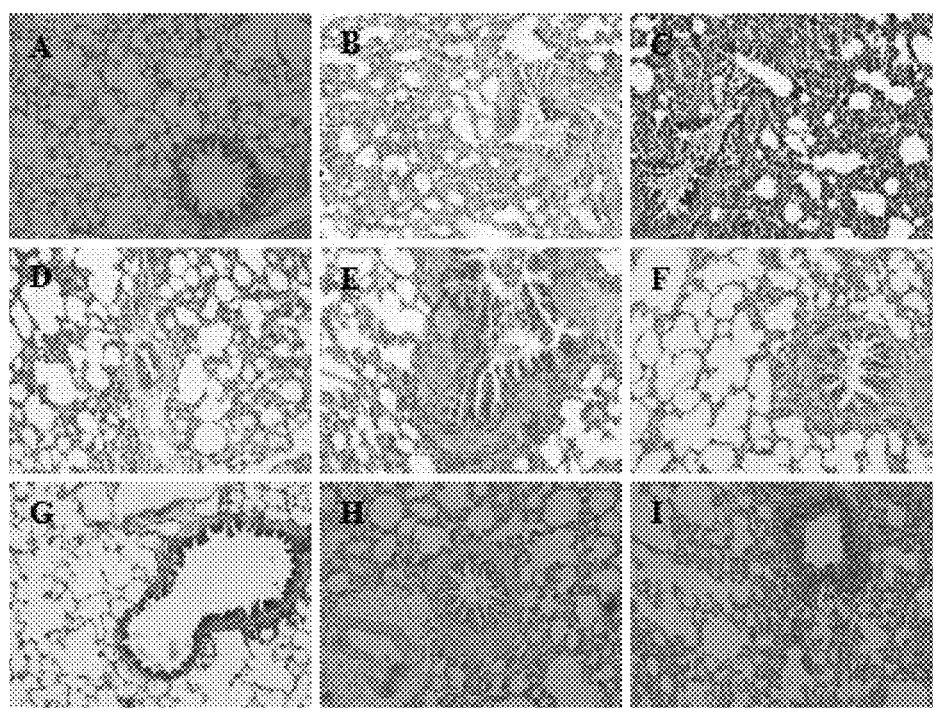
FIG. 3 shows a representative diagram (HE staining, ×200) of the influence of *Asarum* total polysaccharide on lung tissue pathology of guinea pig models with cough hypersensitivity, wherein A is the blank group, B is the model group, C is the solvent group (mass fraction 0.5% CMC-Na), D is the codeine phosphate 30 mg/kg group, E is the *Asarum* total polysaccharide 200 mg/kg group, F is the *Asarum* total polysaccharide 400 mg/kg group, G is the *Asarum* total polysaccharide 800 mg/kg group, H is the total *Asarum* extract 1600 mg/kg group, and I is the *Asarum* total volatile oil 200 mg/kg group.

(5) Observation on Influence of *Asarum* Total Polysaccharide Extract on Pathology of Lung Tissues and Tracheal Tissues of Guinea Pig Models with Cough Hypersensitivity The pathological results of lung tissues of animals in each group after CS-exposure and medicine intervention are as shown in FIG. 3. The figures show that bronchi, alveoli, accompanying arterioles of guinea pigs in a normal group (FIG. 3A) are complete in structure; the ciliated epithelia of the airway are arranged in order; there is no inflammatory cell for infiltration around bronchi and blood vessels, and no hyperemia and edema. Compared with the normal control group, the lung tissues of guinea pigs in the model group (FIG. 3B) show typical pathological inflammatory changes that the bronchial mucosal epithelium cilia are in a lodging state, the bronchial walls are infiltrated by a large number of inflammatory cells, the alveolar septa are widened, the alveolar structure is disordered, and some alveolar septa are fractured. Pathological changes of the lung tissues in the solvent group (FIG. 3C) are almost the same as those in the model group. Compared with the model group, the pathology of the lung tissues of guinea pig in the high-, medium- and low-dosage groups of *Asarum* total polysaccharide (FIG. 3E, F, G) is improved to different degrees, wherein the improvement of the high-dosage group is the most obvious; the bronchial and alveolar structures are almost complete; the bronchial cilia have no obvious lodging; the airway epithelial structure is almost complete; and the infiltration of inflammatory cells around the lung tissues and the blood vessels is reduced obviously. In the medium-dosage group, the alveolar septa are slightly widened; and there are a small amount of inflammatory cells for infiltration around the bronchi and the blood vessels. In the low-dosage group, the bronchial and alveolar structures are damaged; the airway cilia are in lodging state; and the infiltration of inflammatory cells around the bronchi and the blood vessels is obvious. Compared with the model group, the pathology of the lung tissues in the *Asarum* total extract group (FIG. 3H) and the *Asarum* total volatile oil group (FIG. 3I) is also improved greatly; and the bronchial wall structure is almost complete. In the total extract group, there are only a very small amount of inflammatory exudates in the bronchial lumina; in the total volatile oil group, there is almost no inflammatory exudate in the bronchial luma; there are a small amount of inflammatory cells for infiltration around the bronchi and the blood vessels; the improvement degrees of the pathology of the lung tissues in the both are substantially the same as that of the medium-dosage group of *Asarum* total polysaccharide. Compared with the model group, the pathology of the lung tissues in the codeine phosphate group (FIG. 3D) is also improved; the alveolar septa are widened; and the infiltration of inflammatory cells around the bronchi and the blood vessels is reduced.

Figure 4:
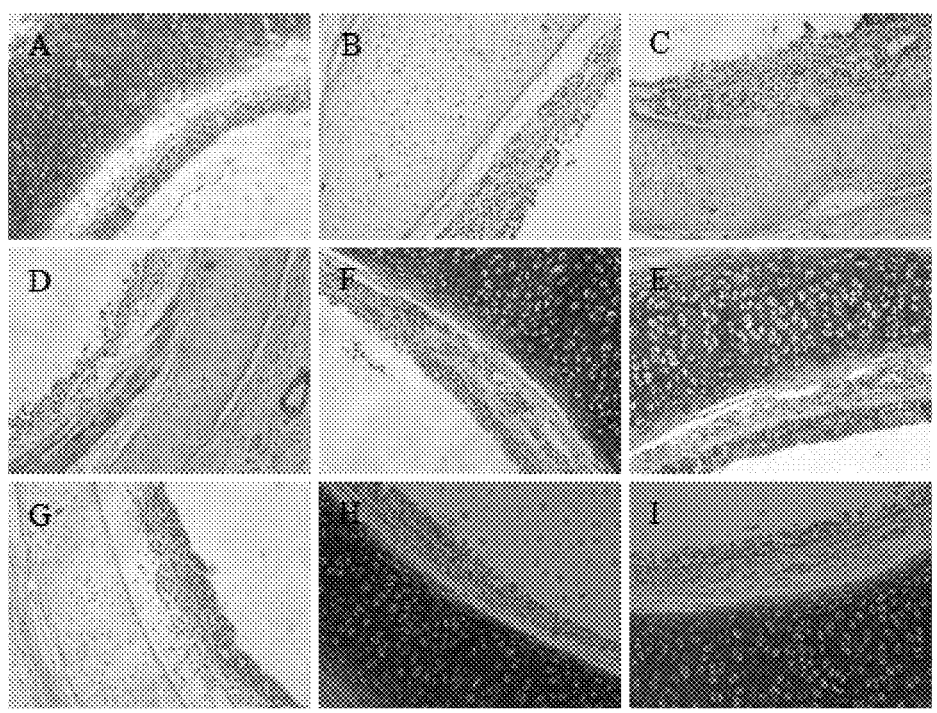
FIG. 4 shows the representative diagram (HE staining, ×200) of the influence of *Asarum* total polysaccharide on tracheal tissue pathology of guinea pig models with cough hypersensitivity, wherein A is the blank group, B is the model group, C is the solvent group (mass fraction 0.5% CMC-Na), D is the codeine phosphate 30 mg/kg group, E is the *Asarum* total polysaccharide 200 mg/kg group, F is the *Asarum* total polysaccharide 400 mg/kg group, G is the *Asarum* total polysaccharide 800 mg/kg group, H is the total *Asarum* extract 1600 mg/kg group, and I is the *Asarum* total volatile oil 200 mg/kg group.

The observation on the tracheal pathology of animals in each group after CS-exposure and medicine intervention is as shown in FIG. 4. The figures show that the tracheal epithelia of guinea pigs in the normal group (FIG. 4A) are complete; the tracheal lumina are regular; the tracheal walls are not thickened; cilia are arranged in order; and there is almost no infiltration of inflammatory cells. Compared with the normal control group, tracheae of the guinea pigs in the model group (FIG. 4B) show typical pathological inflammatory changes that tracheal mucosal epithelium cilia are in the lodging state, the mucosal epithelial cells fall off, the tracheal walls are infiltrated by a large number of inflammatory cells, and the basement membranes are thickened in different degrees. The tracheal pathological changes of the solvent group (FIG. 4C) are almost the same as those of the model group. Compared with the model group, the tracheal pathology of guinea pigs in the high-, medium- and low-dosage groups of *Asarum* total polysaccharide (FIG. 4E, F, G) is improved in different degrees; the tracheal epithelium structure is almost complete; the basement membrane has no obvious hyperplasia; the exudates in the lumina are reduced; the cilia are arranged regularly; and there is no obvious infiltration of inflammatory cells, wherein the improvement of the high-dosage group is the most obvious. Compared with the model group, the pathology of the tracheal tissues in the *Asarum* total extract group (FIG. 4H) and the *Asarum* total volatile oil group (FIG. 4I) is also improved; the airway epithelial cilia are in a slight lodging state; the basement membrane is not obviously thickened; the tracheal walls are infiltrated by a small amount of inflammatory cells; and the improvement degrees of tracheal tissue pathology of the both are slightly worse than that of the medium-dosage group of *Asarum* total polysaccharide. The tracheal pathology in the codeine phosphate group (FIG. 4D) is almost the same as that in the model group, and is not improved obviously.

Embodiment 6

Taking the *Asarum* total polysaccharide extract prepared according to the method of the Embodiment 1, adding distilled water for dissolution, adding simple syrup to be more than 50% of the sugar content, adding 0.3% of sodium benzoate and ethylparaben, mixing the mixture uniformly, boiling and filtering the mixture immediately, adding distilled water to a predetermined amount, and sub-packaging the mixture to obtain *Asarum* total polysaccharide cough syrup.

Embodiment 7

Taking 800 g of *Asarum* total polysaccharide extract prepared according to the method of the Embodiment 1 and 40 g of aerosil; screening the materials with the sieve of 60 meshes; mixing the screened materials fully and uniformly; adding 24 g of magnesium stearate; mixing; conducting dry granulation; screening the obtained granules with the sieve of 40 meshes; and filling the screened granules to form capsules.

Embodiment 8

Antitussive Effect of Different *Asarum* Polysaccharide Extracts on Guinea Pig Models with Cough Hypersensitivity Experimental materials are same as those of the Embodiment 5. The animals are grouped as follows: the blank group and the model group (1 mL/kg of saline), the solvent group (CMC-Na aqueous solution with the mass percentage concentration of 0.5%), the positive medicine group (30 mg/kg of codeine phosphate), a group of the *Asarum* total polysaccharide extract prepared in the prior art (800 mg/kg, the preparation method comprises the following steps: cutting the roots of *Asarum Heterotropoides* Fr. Schmidt var. *Mandshuricum* (Maxim.) Kitag. into pieces, adding 20 times amount of distilled water to soak the cut roots overnight, extracting decoction from boiling water for 6 hours, filtering the decoction with four layers of gauze, repeatedly decocting filter residues twice, 6 hours each time, combining the filtrates, concentrating the filtrate to 1000 ml, precipitating with 80% of ethanol, centrifuging (4500 r/m, 10 min), and conventionally drying the precipitates (washing the precipitates three times with each of ethanol and ether) to obtain coarse *Asarum* polysaccharides (Li Jingjing, Study on the Separation, Purification and Immunological Activity of Polysaccharide from *Asarum* heterotropoides, Journal of Changchun Normal University (Natural Science), 2008, 27(1): 54-58)), a group of the *Asarum* total polysaccharides extract in the Embodiment 1 (800 mg/kg), and a group of the *Asarum* total polysaccharide extract in the Embodiment 2 (800 mg/kg). The rest of experimental methods are same as the Embodiment 5. Experimental results show that the *Asarum* total polysaccharides prepared in the prior art, the Embodiment 1 and the Embodiment 2 can significantly reduce the cough frequency of guinea pigs (see Table 7), prolong the cough latent period of guinea pigs, and also reduce the ratio of Neu in BALF of the guinea pigs, wherein the *Asarum* total polysaccharide prepared in the Embodiment 2 has the best effect, and the *Asarum* total polysaccharides prepared in the prior art also have antitussive activity, but do not get effect much better than the total polysaccharides prepared in the present invention.

TABLE 7

Influence (mean +/− s, n = 8) of different *Asarum* total polysaccharide extracts on the cough frequency of guinea pig models with cough hypersensitivity

| Group | Dose (mg/kg) | Cough frequency (times) | Antitussive rate (%) |
|---|---|---|---|
| Blank control | — | 19.4 +/− 2.6** | — |
| Model group | — | 30.2 +/− 2.7 | — |
| Solvent control | — | 32.0 +/− 3.2 | — |
| Codeine phosphate | 30 | 5.7 +/− 1.9*** | 81.1 |
| *Asarum* total polysaccharide prepared in the prior art | 800 | 10.7 +/− 1.4*** | 64.6 |
| *Asarum* total polysaccharide in the Embodiment 1 | 800 | 8.8 +/− 3.6*** | 70.9 |
| *Asarum* total polysaccharide in the Embodiment 2 | 800 | 8.2 +/− 1.4*** | 72.8 |

Note:
compared with the model group,
**$p < 0.01$,
***$p < 0.001$.

The technical features of all the above embodiments may be combined arbitrarily. In order to make the description concise, all possible combinations of all the technical features in the above embodiments are not described one by one. However, as long as there is no contradiction in the combinations of these technical features, all the combinations should be considered within the scope of the disclosure contained in the present description.

The above embodiments only express some embodiments of the present invention, are described more specifically and in detail, but shall not be understood as a limitation to the scope of the invention patent. It should be noted that those skilled in the art can also make several modifications and improvements, which belong to the protection scope of the present invention, without departing from the concept of the present invention. Therefore, appended claims shall prevail in the protection scope of the invention patent.

What is claimed is:

1. A method of treating cough, comprising:
administering an effective amount of a composition comprising *Asarum* total polysaccharides to a subject in need thereof, wherein the *Asarum* total polysaccharides are prepared by the following steps:
   a. subjecting roots and/or rhizomes of *Asarum* to a heat reflux using water;
   b. concentrating and drying under vacuum to produce an *Asarum* total extract;
   c. dissolving the *Asarum* total extract in water to produce an *Asarum* total extract solution and adding 60-99% ethanol by volume into the *Asarum* total extract solution to completely precipitate to produce a supernate and a precipitate;
   d. discarding the supernate and filtering the precipitate under vacuum;
   e. washing the filtered precipitate with 60-100% ethanol by volume and drying under vacuum to obtain the *Asarum* total polysaccharides.

2. The method of claim 1, wherein the cough is chronic cough.

3. The method of claim 1, wherein the content of polysaccharides in the *Asarum* total polysaccharides is 60-80 wt %.

4. The method of claim 1, wherein the composition further comprises a pharmaceutically acceptable carrier.

5. The method of claim 4, wherein the pharmaceutically acceptable carrier is selected from the group consisting of a filler, a binder, a lubricant, a disintegrant and a wetting agent.

6. The method of claim 4, wherein a formulation of the composition is selected from the group consisting of granule, tablet, capsule, pill, dripping pill, effervescent tablet, ointment, syrup, injection, oral liquid, mixture, tincture, sustained-release preparation, controlled-release preparation and targeting preparation.

7. The method of claim 1, wherein the *Asarum* is selected from *Asarum Heterotropoides* Fr. Schmidt var. *Mandshricum* (Maxim.) Kitag., *Asarum sieboldii* Miq. var. seoulense Nakai or *Asarum sieboldii* Miq.

\* \* \* \* \*